US00PP20599P2

(12) United States Plant Patent
Dekker

(10) Patent No.: US PP20,599 P2
(45) Date of Patent: Dec. 22, 2009

(54) ***CHRYSANTHEMUM* PLANT NAMED 'DEKRINGA YELLOW'**

(50) Latin Name: *Chrysanthemum×morifolium*
Varietal Denomination: Dekringa Yellow

(75) Inventor: Cornelis W. Dekker, Hensbroek (NL)

(73) Assignee: Dekker Breeding B.V., Hensbroek (NL)

( * ) Notice: Subject to any disclaimer, the term of this patent is extended or adjusted under 35 U.S.C. 154(b) by 0 days.

(21) Appl. No.: 12/287,355

(22) Filed: Oct. 8, 2008

(51) Int. Cl.
*A01H 5/00* (2006.01)

(52) U.S. Cl. ..... Plt./295

(58) Field of Classification Search ..... Plt./295
See application file for complete search history.

*Primary Examiner*—Kent L Bell
(74) *Attorney, Agent, or Firm*—C. A. Whealy

(57) ABSTRACT

A new and distinct cultivar of *Chrysanthemum* plant named 'Dekringa Yellow', characterized by its single-type inflorescences with bright yellow-colored ray florets; strong and upright flowering stems; moderately vigorous growth habit; freely flowering habit; early and uniform flowering response; and good postproduction longevity.

2 Drawing Sheets

Botanical designation: *Chrysanthemum×morifolium.*
Cultivar denomination: 'Dekringa Yellow'.

BACKGROUND OF THE INVENTION

The present invention relates to a new and distinct cultivar of *Chrysanthemum* plant, botanically known as *Chrysanthemum×morifolium*, commercially grown as a cut flower and hereinafter referred to by the name 'Dekringa Yellow'.

The new *Chrysanthemum* is a naturally-occurring whole plant mutation of *Chrysanthemum×morifolium* 'Dekringabronze', disclosed in U.S. Plant Pat. No. 19,344. The new *Chrysanthemum* was discovered and selected by the Inventor as a single flowering plant from within a population of plants of 'Dekringabronze' in a controlled greenhouse environment in Hensbroek, The Netherlands in October, 2006.

Asexual reproduction of the new *Chrysanthemum* by terminal cuttings in a controlled greenhouse environment in Hensbroek, The Netherlands since November, 2006, has shown that the unique features of this new *Chrysanthemum* are stable and reproduced true to type in successive generations.

SUMMARY OF THE INVENTION

Plants of the new *Chrysanthemum* have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Dekringa Yellow'. These characteristics in combination distinguish 'Dekringa Yellow' as a new and distinct cultivar of *Chrysanthemum:*

1. Single-type inflorescences with bright yellow-colored ray florets.
2. Strong and upright flowering stems.
3. Moderately vigorous growth habit.
4. Freely flowering habit.

5. Early and uniform flowering response; plants flower about 37 days after the start of photoinductive treatments.
6. Good postproduction longevity; plants maintain good substance for about four weeks in an interior environment.

Plants of the new *Chrysanthemum* differ from plants of 'Dekringabronze' primarily in ray floret color as plants of 'Dekringabronze' have bronze-colored ray florets.

Plants of the new *Chrysanthemum* can be compared to plants of *Chrysanthemum×morifolium* 'Dektanga Pink', disclosed in U.S. Plant Pat. No. 18,903. In side-by-side comparisons conducted in Hensbroek, The Netherlands, plants of the new *Chrysanthemum* differed from plants of 'Dektanga Pink' in the following characteristics:

1. Plants of the new *Chrysanthemum* were more vigorous than plants of 'Dektanga Pink'.
2. Plants of the new *Chrysanthemum* were more freely branching than plants of 'Dektanga Pink'.
3. Plants of the new *Chrysanthemum* and 'Dektanga Pink' differed in ray floret color as plants of 'Dektanga Pink' had pink-colored ray florets.
4. Plants of the new *Chrysanthemum* had larger ray florets than plants of 'Dektanga Pink'.

BRIEF DESCRIPTION OF THE PHOTOGRAPHS

The accompanying colored photographs illustrate the overall appearance of the new *Chrysanthemum.* These photographs show the colors as true as it is reasonably possible to obtain in colored reproductions of this type. Colors in the photographs may differ slightly from the color values cited in the detailed botanical description which accurately describe the colors of the new *Chrysanthemum.*

The photograph on the first sheet comprises a side perspective view of a typical flowering stem of 'Dekringa Yellow' grown as a spray type.

The photograph on the second sheet comprises close-up views of the upper (top of photograph) and lower surfaces (bottom of photograph) of typical inflorescences and leaves of 'Dekringa Yellow'.

DETAILED BOTANICAL DESCRIPTION

The aforementioned photographs and following observations and measurements describe plants grown during the late summer in Hensbroek, The Netherlands, under commercial practice in a glass-covered greenhouse. Plants were initially given two weeks of long day/short night treatments followed by short day/long night treatments to induce flower initiation and development. During the production of the plants, day temperatures ranged from 18° C. to 25° C., night temperatures ranged from 20° C. to 22° C. and light levels were about 7 kilolux. Plants were pinched one time and were 7.5 weeks from planting when the photographs and the description were taken. In the following description, color references are made to The Royal Horticultural Society Colour Chart, 2001 Edition, except where general terms of ordinary dictionary significance are used.

Botanical classification: *Chrysanthemum×morifolium* 'Dekringa Yellow'.

Parentage: Naturally-occurring whole plant mutation of *Chrysanthemum×morifolium* 'Dekringabronze', disclosed in U.S. Plant Pat. No. 19,344.

Propagation:

*Type.*—Terminal vegetative cuttings.

*Time to initiate roots, summer.*—About six days at 20° C.

*Time to initiate roots, winter.*—About seven days at 20° C.

*Time to produce a rooted young plant, summer.*—About 13 days at 20° C.

*Time to produce a rooted young plant, winter.*—About 15 days at 20° C.

*Root description.*—Fine, fibrous; light brown in color.

*Rooting habit.*—Freely branching, moderately dense.

Plant description:

*Appearance/growth habit.*—Herbaceous single-type cut flower that is typically grown as a spray-type. Moderately vigorous growth habit.

*Flowering stem description.*—Aspect: Erect. Length: About 65 cm. Spray diameter: About 10 cm to 15 cm. Lateral branch length: About 12 cm to 20 cm. Lateral branch diameter: About 5 mm to 6 mm. Internode length: About 1.5 cm to 2 cm. Strength: Strong. Texture: Finely pubescent; longitudinally ridged. Color: Close to 146B to 146C.

*Foliage description.*—Arrangement: Alternate; simple. Length: About 5.5 cm to 8.5 cm. Width: About 2.5 cm to 4 cm. Apex: Cuspidate. Base: Attenuate. Margin: Palmately lobed; sinuses divergent. Texture, upper and lower surfaces: Pubescent, slightly rough; veins prominent on lower surface. Venation pattern: Pinnate, reticulate. Color: Developing leaves, upper surface: Close to 146B to 146B. Developing leaves, lower surface: Close to 138B. Fully developed leaves, upper surface: Close to 147A; venation, close to 146A. Fully developed leaves, lower surface: Close to 147B; venation, close to 146B. Petiole: Length: About 7 mm to 12 mm. Diameter: About 2 mm to 4 mm. Texture, upper and lower surfaces: Slightly rough. Color, upper and lower surfaces: Close to 146B.

Inflorescence description:

*Appearance.*—Single-type inflorescence form with oblong-shaped ray florets. Inflorescences borne on terminals, arising from leaf axils. Ray and disc florets develop acropetally on a capitulum. Inflorescences slightly fragrant.

*Flowering response.*—Under natural conditions, plant flower in the autumn/winter in the Northern Hemisphere. At other times of the year, inflorescence initiation and development can be induced under short day/long night conditions (at least 13.5 hours of darkness). Early and uniform flowering response; plants exposed to eight days of long day/short night conditions after planting followed by photoinductive short day/long night conditions flower about 37 days later when grown as a spray-type.

*Postproduction longevity.*—In an interior environment, inflorescences and foliage will maintain good color and substance for about four weeks; inflorescences persistent.

*Quantity of inflorescences.*—Freely flowering habit; when grown as a spray type, about 55 inflorescences per flowering stem develop.

*Inflorescence size.*—Diameter: About 2.5 cm. Depth (height): About 1.5 cm. Disc diameter: About 7 mm to 9 mm. Receptacle height: About 2.5 mm. Receptacle diameter: About 2.5 mm. Receptacle color: Close to 145B to 145C.

*Inflorescence buds.*—Shape: Flattened spherical. Height: About 2 mm to 3 mm. Diameter: About 4 mm to 5 mm. Color: Close to 137C.

*Ray florets.*—Length: About 9 mm to 14 mm. Width: About 5 mm to 7 mm. Shape: Oblong. Apex: Emarginate. Base: Attenuate. Margin: Entire. Angle: Initially upright to close to about 45° from vertical. Texture, upper and lower surfaces: Smooth, glabrous; satiny. Number per inflorescence: About 15 to 20 arranged in about two whorls. Color: When opening, upper surface: Close to 7A. When opening, lower surface: Close to 6C. Fully opened, upper surface: Close to 7A; color becoming closer to 7C with development. Fully opened, lower surface: Close to 7D.

*Disc florets.*—Shape: Fused tubular, elongated. Apex: Dentate. Length: About 3 mm to 5 mm. Diameter: About 1 mm to 2 mm. Number per inflorescence: About 150, massed at the center. Color, immature: Apex: Close to 154A. Mid-section and base: Close to 145C. Color, mature: Apex: Close to 6A. Mid-section and base: Close to 145D.

*Involucral bracts.*—Length: About 6 mm to 7 mm. Width: About 2 mm to 4 mm. Shape: Ovate. Apex: Obtuse. Base: Truncate. Margin: Entire. Texture, upper surface: Smooth, glabrous. Texture, lower surface: Pubescent; rough. Number per inflorescence: About 18 arranged in about two whorls. Color, upper surface: Close to 137C. Color, lower surface: Close to 137B.

*Peduncles.*—Length: About 5 cm to 7.5 cm. Diameter: About 1.5 mm to 2 mm. Angle: Erect to about 30° from vertical. Strength: Moderately strong to strong. Texture: Pubescent; longitudinally ridged. Color: Close to 146A to 146B.

*Reproductive organs.*—Androecium: Not observed. Gynoecium: Present on both ray and disc florets. Style length: About 3 mm. Style color: Close to 145D. Stigma color: Close to 6A.

*Seed/fruit.*—Seed and fruit production has not been observed.

Disease/pest resistance: Resistance to pathogens and pests common to *Chrysanthemums* has not been observed on plants grown under commercial conditions.

It is claimed:

1. A new and distinct *Chrysanthemum* plant named 'Dekringa Yellow' as illustrated and described.

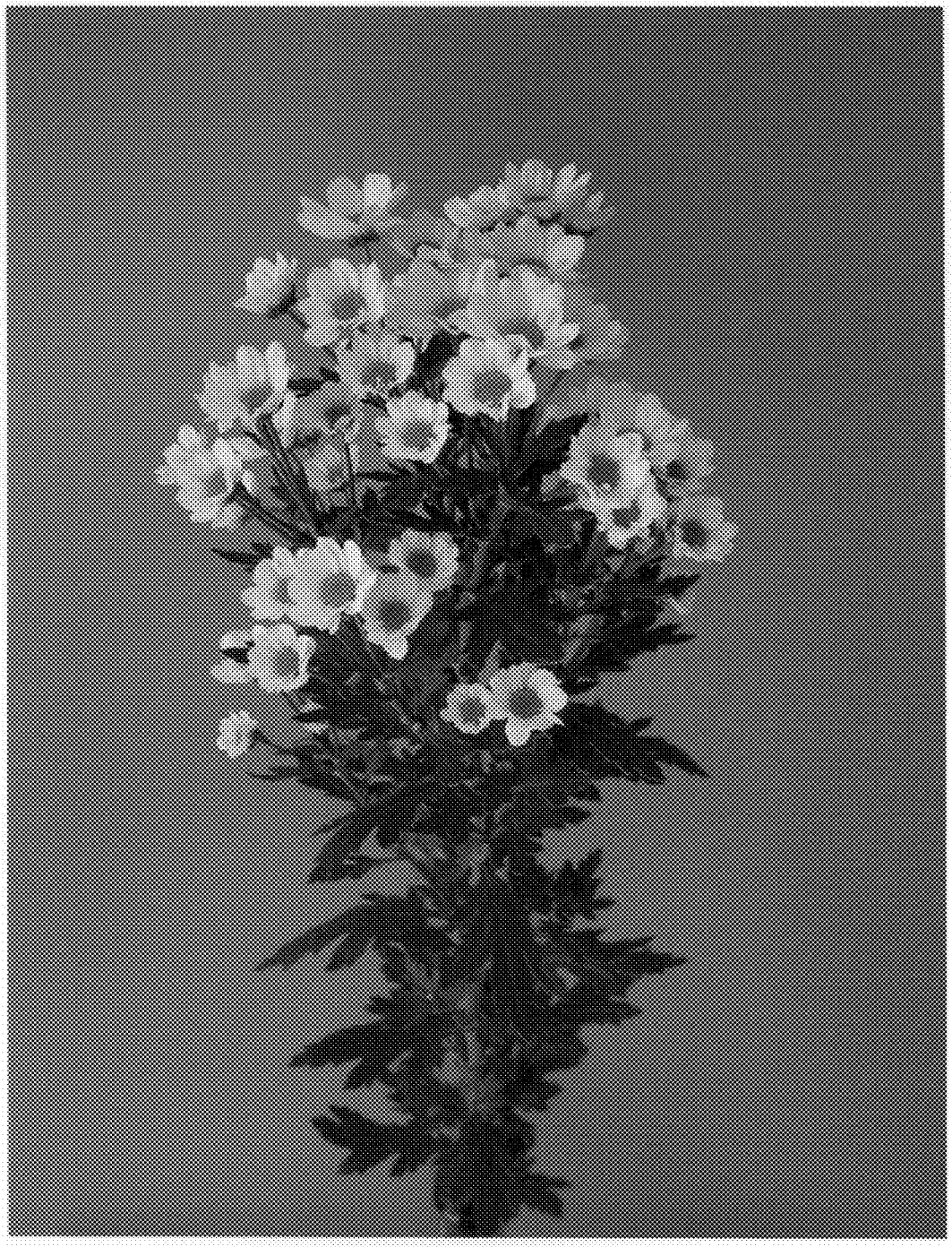

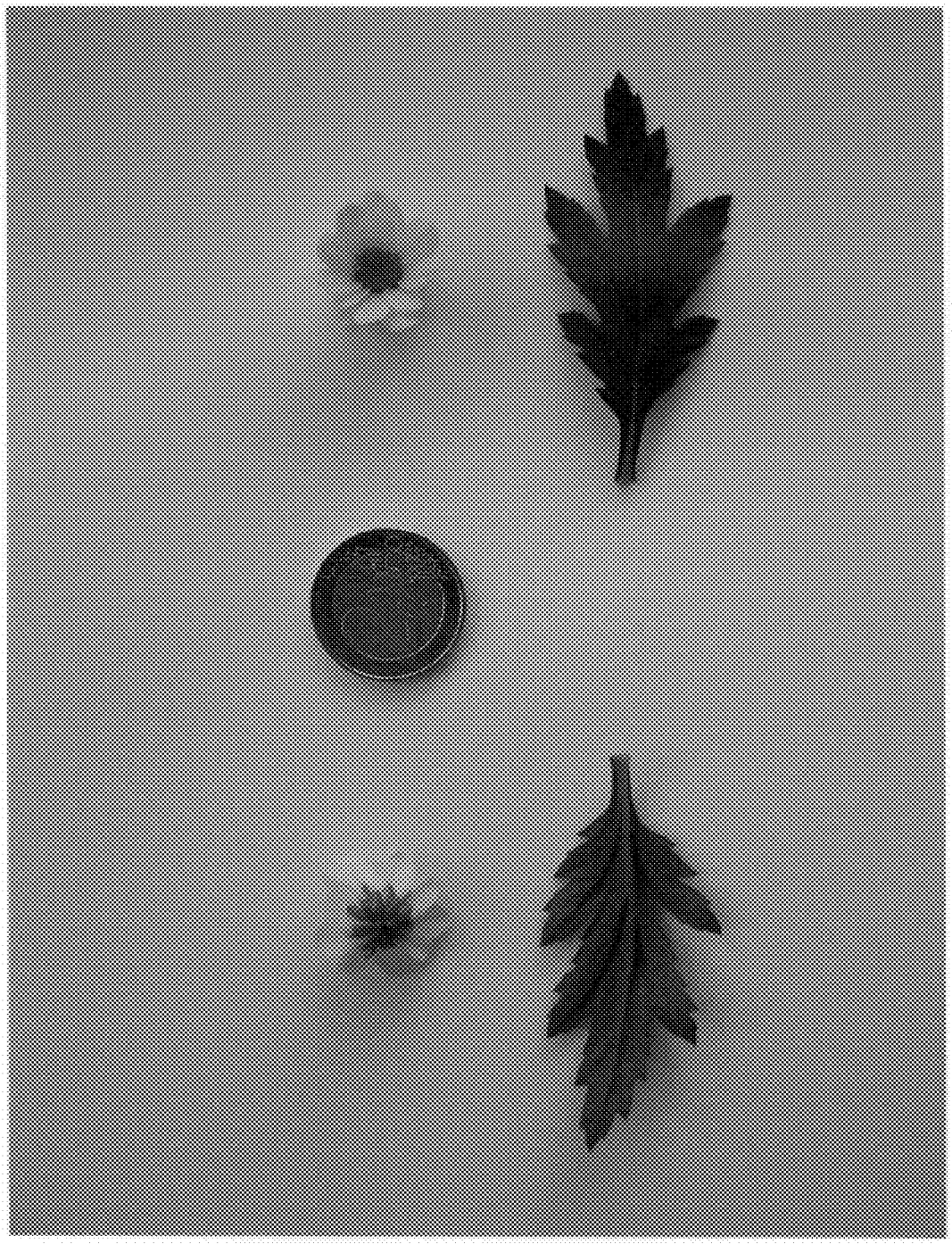

* * * * *